Figure 1:
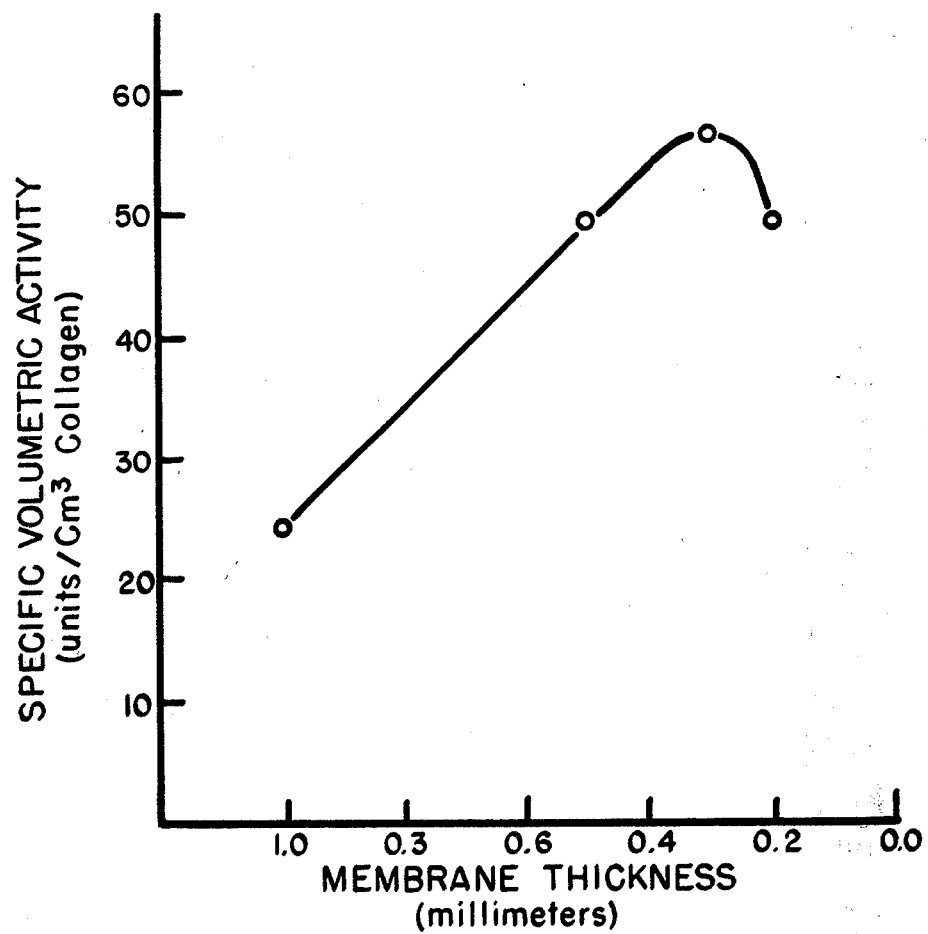

United States Patent [19]

Jefferies et al.

[11] 4,409,332
[45] Oct. 11, 1983

[54] COLLAGEN-ENZYME CONJUGATES THAT EXHIBIT NO INFLAMMATORY RESPONSE AND METHOD FOR MAKING THE SAME

[76] Inventors: Steven R. Jefferies, 5802 Leith Walk, Baltimore, Md. 21239; James L. Gutmann, 10112 Daventry Dr., Cockeysville, Md. 21030; Barry M. Heatfield, 33 Penny La., Baltimore, Md. 21209

[21] Appl. No.: 338,973

[22] Filed: Jan. 12, 1982

[51] Int. Cl.³ .............................................. C12N 9/96
[52] U.S. Cl. .................................. 435/188; 260/123.7
[58] Field of Search ...................... 435/188; 260/123.7

[56] References Cited

U.S. PATENT DOCUMENTS

| | | | |
|---|---|---|---|
| 2,900,644 | 8/1959 | Rosenburg et al. | 3/1 |
| 3,093,439 | 6/1963 | Rothwell | 8/94.11 |
| 3,823,212 | 7/1974 | Chvapil | 260/123.7 X |
| 3,833,746 | 9/1974 | Cohly | 260/123.7 X |
| 3,843,446 | 10/1974 | Vieth et al. | |
| 4,123,384 | 10/1978 | Hundt et al. | 435/188 |
| 4,193,813 | 3/1980 | Chvapil | 260/123.7 X |
| 4,223,984 | 9/1980 | Miyata et al. | 260/123.7 X |
| 4,260,228 | 4/1981 | Miyata | 260/123.7 |
| 4,323,647 | 4/1982 | Monji et al. | 435/188 X |

OTHER PUBLICATIONS

"Surgikos", Johnson & Johnson, Jul. 1975, pp. 1 & 2.
"Periodontal Disease", Sep. 1978, pp. 463-464.
"Avitene", Avicon Inc., 9-1976, pp. 29985-29986.
"Alkaline Phosphatase", Chapter 12, pp. 865-907, (1979), McComb et al.
Anderson, Journ. of Biomedical Materials Research, pp. 889-901, (1981).
Bradley et al., Biomat. Med. Dev. Art. Org., 5(2), pp. 159-175, (1977).
"Inflammation: Mechanisms and Treatment", Feb. 18-22, 1980, Williams et al., pp. 787-788.
Biomat. Med. Dev. Art. Org., 5(4), 337-354, (1977), Jefferies et al.
Wound Healing & Wound Infection, (Hunt ed.), 1980, pp. 194-207.
Repair and Regeneration (Dunphy editor), 1969, pp. 263-285.
Calcif. Tissue Int. 31, 257-259, (1980), Marino et al.
J. of Biomedicals Material Res., vol. 16, 245-263, (1982), Chvapil.
Progress in Cardiovascular Diseases, vol. XXIII, No. 2, 1980, pp. 141-166, Angell.

*Primary Examiner*—Howard E. Schain
*Attorney, Agent, or Firm*—Cushman, Darby & Cushman

[57] ABSTRACT

Collagen polymers are rendered non-inflammatory by complexation with alkaline phosphatase according to the procedure disclosed. Applications of these non-inflammatory collagen complexes include the production of non-inflammatory collagen sutures, collagen soft tissue replacements including wound and burn coverings and arterial vessel replacements, collagen drug delivery devices, and vitreous replacement for opthalmologic therapy. Gels composed of the collagen-alkaline phosphatase conjugate plus calcium hydroxide are useful as an agent in endodontic therapy. Structural durability and stabilization of the anti-inflammatory properties of the material are enhanced by crosslinking with glutaraldehyde or other crosslinking agents. Glutaraldehyde also acts to sterilize and disinfect the collagen conjugate prior to in-vivo use.

11 Claims, 3 Drawing Figures

COLLAGEN-ENZYME CONJUGATES THAT EXHIBIT NO INFLAMMATORY RESPONSE AND METHOD FOR MAKING THE SAME

BACKGROUND OF THE INVENTION

This invention relates to a biocompatible, non-inflammatory, collagen conjugate material, described herein in the form of a porous membrane structure, and to a process for making this material. While individual components of this system are known in the art and in the related literature, described herein is a novel composite material, able to alter and totally eliminate the mild, chronic cellular inflammatory response exhibited by purified bovine corium collagen. The novel conjugate collagen material herein described maintains its complete physical integrity for an extended period of time, up to at least 3 months, in the absence of any inflammatory response when implanted subcutaneously in animal models.

Collagen is used in medicine and dentistry in a variety of configurations and uses. Resorbable collagen suture material in the form of plain or chromic surgical gut is one of the most widely used surgical suture materials in the world. Within the last decade, Surgikos, a Johnson & Johnson Company, introduced the bovine collagen Artegraft to serve as a substitute segmental arterial replacement, as an arterial bypass, or as an arteriovenous shunt. In 1976, Avicon, Inc. introduced Avitene, an absorbable microfibrillar collagen hemostat for use in oral and general surgery. More experimental uses of collagen have included the use of collagen gels as a vitreous replacement in ophthalmologic surgery, and the use of reconstituted collagen membranes as a wound dressing in burn patients.

One repeatedly documented drawback to the use of collagen as a biomaterial is the consistent chronic cellular inflammatory response evident in both animal and human studies. Avitene, as described in its package insert, has been shown to stimulate a mild chronic cellular inflammatory response in both human and animal studies. The literature reports that collagen sutures are the most irritating and among those eliciting the greatest giant cell response; see Schluger, et. al., *Periodontal Disease*, pg 464, Lea & Febiger, 1978. This inflammatory response may result in residual scar tissue formation or even, in general surgery, in adhesion formation. This drawback must be compared with the advantages of this suture material, which include its monofilament-like structure resulting in ease of handling, uniform tensile strength, and uniform predictable rates of absorption.

The significance of this low-grade inflammatory response associated with the use of collagen as a biomaterial can be illustrated by some of the adversed reactions reported with its use. Avitene, for example, when placed in close approximation to the closure of skin incisions may interfere with the healing of skin edges. Adverse reactions associated with the Artegraft suture material include pseudointima formation and, less frequently, pseudodiaphragm formation. Disruption of anastomoses, especially in the presence of infection, has also been observed. In a few cases transient low grade fever, the etiology of which has not been obvious, has been experienced. The inflammatory reaction to the Artegraft collagen may be associated with the occasional true aneurysm reported with its use, since this inflammatory response may accelerate the degradation of the fibrous collagen making up the structural support of the Artegraft.

Clearly, it would be extremely advantageous for any biomaterial to be non-inflammatory. Few synthetic biomaterials possess this property. Since collagen possesses many worthwhile properties as a biomaterial, not the least of which is its structural similarity to native connective tissue, the elimination of the low-grade inflammatory response connected with its use would be highly desirable.

The other major component of the conjugate described herein is the enzyme alkaline phosphatase. When our experiments with the compexation of collagen-alkaline phosphatase membranes began, the intent was to induce calcification within these membranes as it has been hypothesized that alkaline phosphatase has some major role in calcification. Recently, a comprehensive review of all the literature concerning the structure and function of alkaline phosphatase has become available; see McComb, R. B., & Bowers, G. M., *Alkaline Phosphatase*, Plenum Press, New York, N.Y., 1979. In a section devoted to physiological functions of the enzyme, the authors state: "Although the hydrolytic functions of alkaline phosphatase have been intensively studied for more than 50 years, we have at this time no clear idea of the value of this enzyme to the organism."

While an increase in the alkaline phosphatase activity of host leukocytes is associated with an increase in phagocytic activity, the significance of this phenomenon is not well understood. Granule-bound enzymes, including alkaline phosphatase, are released during the phagocytic process. In addition, the administration of steroids induces an increase in cellular alkaline phosphatase. The significance of this observation is also highly speculative.

In summary, based on the information available to us prior to making the invention herein disclosed, there was little if any reason to suspect the in-vivo activity of the novel biomaterial described below.

SUMMARY OF THE INVENTION

We have found that a complex of reconstituted collagen with soluble alkaline phosphatase, crosslinked with glutaraldehyde, UV radiation, or gamma radiation, when fabricated into membrane-like structures and implanted subcutaneously into experimental animal models substantially completely eliminates, and in most cases totally eliminates, the inflammatory response observed with collagen membranes not complexed with the enzyme alkaline phosphatase. Accordingly our invention includes, as a novel composition of matter, complexes or conjugates of reconstituted collagen with alkaline phosphatase, membrane-like structures and gels fabricated from these complexes and methods for preparing such complexes.

The complexes of our invention are suitable for numerous applications including the production of noninflammatory collage sutures, collagen soft tissue replacements including wound and burn coverings and arterial vessel replacements as well as vitreous replacement for ophthalmologic therapy to name illustrative end uses. Indeed virtually any situation in which collagen is a preferred biomaterial and the control of the inflammatory response is critical to the success of the material or device provides a suitable environment for the use of these compositions and structures.

While a majority of our experimental work with the collagen conjugate is in a membrane form, such complexes are also conveniently fashioned into a variety of other forms, including gels, sponge-like structures, nonofilament fibers, and tubular structures.

Proportions of alkaline phosphatase complexed with the collagen matrix can vary from about 0.5% to about 3% by weight, with optimal concentration being about 1.5% by weight. A majority, i.e., more than 50% by weight of the conjugate material is collagen; the balance is water. The glutaraldehyde concentration, when the same is used for crosslinking, can vary from about 0.2% by weight to about 5% by weight for varying periods of time. The optimal crosslinking conditions for glutaraldehyde crosslinking are 0.5% by weight glutaraldehyde buffered at pH 8.7 for a duration of 20 minutes at 22° C. The cross-linking of reconstituted collagen with glutaraldehyde and demineralized bone particles and/or solubilized bone morphogenic protein is described in copending application Ser. No. 304,367 filed Sept. 21, 1981, in the name of Steven R. Jefferies; the disclosure of this application is incorporated herein by reference.

The amount of enzyme complexed and the degree of crosslinking controls the inflammatory response of the biomaterial in-vivo and the rate of resorption of the implant.

The invention will now be further described with reference to the following examples, considered illustrative but not limiting of the invention. Unless otherwise indicated all parts and percentages are by weight.

EXAMPLE 1

Preparing the collagen/enzyme conjugate: Two grams of Avitene microfibrillar collagen were dissolved in 100 milliliters of 0.1 N NaOH in sterile water under mild stirring. The pH of the collagen dispersion was adjusted to pH 10.5 with the addition of 0.01 N NaOH as needed. After additional agitation with moderate stirring at 4° C., 30 mg of alkaline phosphatase (2.5 I.U./mg, Dog Intestine, Sigma Chemical Co.) was added to the collagen dispersion in 5 milliliter of sterile distilled water. The collagen-alkaline phosphatase dispersion was homogenized for four, 30-second intervals in a Waring blender at 4° C. and then deaerated for 5 hours at 4° C. under a vacuum of 20 inches of mercury. The dispersion was then poured into sterile 15×2 cm petri dishes to depths of 16 millimeters. The petri dishes were covered for 48 hours at a constant temperature of 37° C. in order to promote uniform initial gellation. We have found that too rapid drying in the initial phase of gellation promotes phase separation and leads to a proliferation of entrained air bubbles in the membrane. At the end of 48 hours, the petri dishes covers were removed and drying was allowed to continue at ambient temperatures in a sterile hood.

Cross-linking: After drying, the membranes were removed manually from the petri dishes. A stainless steel circular punch, 6.3 mm in diameter, was used to punch out circular discs of membrane for glutaraldehyde crosslinking. These circular discs were crosslinked in 0.5% glutaraldehyde, pH 8.7 (adjusted with 0.05 M phosphate buffer) for 20 minutes at 22° C. Following crosslinking the membrane discs were washed in 10 batch contacts of stirred sterile normal saline, followed by one contact with 0.005 M glycine and followed by two batch contacts of sterile normal saline. Membranes discs, with a drying thickness of 0.8 mm and a wet thickness of 1 mm, were stored in sterile normal saline at 4° C. prior to animal implantation.

Senstivity testing: Animal implantation studies were conducted with male Spaque-Dawley Rats, 13-14 weeks old, weighing 300 to 350 grams. The rats were anesthetized by ether inhalation; subcutaneous implantation of collagen discs was accomplished in the dorsal subcutaneous tissue by blut dissection. A total of four discs were implanted in each rat; two to the right of the midline, two to the left of the midline.

Four different collagen membrane compositions were evaluated:

System 1—blank collagen membranes (no alkaline phosphatase) which were not crosslinked, System 2—blank collagen membranes (no alkaline phosphatase) which were crosslinked with glutaraldehyde as described above, System 3—collagen membranes complexed with alkaline phosphatase which were not crosslinked System 4—collagen membranes according to the present invention which were complexed with alkaline phosphatase and crosslinked with glutaraldehyde, as indicated above. All incisions were closed with cyanoacrylic tissue adhesive.

All male rats were sacrificed at specific time intervals to allow gross and histologic evaluation of the collagen disc implants. All tissue specimens included at least 7 mm borders of tissue including each of the collagen implants. Specimens were fixed in 4F-1G fixative prior to histologic process. The specimens were mounted in paraffin blocks and histologic sections were cut. These sections were stained with hematoxylin and eosin and observed under low and high power light microscopy. The results of the gross and histologic examinations were as follows: At the time of removal of all soft tissue sections, the specimens were cut across the diameter of the collagen disc implant. This cut cross-section allowed physical inspection of soft tissue-implant interface.

Gross inspection: Each system of implants was inspected over a time period of three to ten weeks of in-vivo implantation revealed the following results:

System 1—The blank, uncrosslinked collagen membranes were indistinguishable from the surrounding connective tissue upon visual inspection in all samples ranging from 3 to 10 weeks.

System 2—Glutaraldehyde crosslinked, blank collagen membranes were distinguishable but adherent to the surrounding connective tissue. The borders of the collagen implant seemed somewhat larger, possibly due to increased localized edema. This swelling of the graft material was more obvious in paraffin sectiosn of the graft material.

System 3—The uncrosslinked collagen-alkaline phosphatase membrane was indistinguishable from the surrounding connective tissue in all samples ranging from 3 to 10 weeks.

System 4—Glutaraldehyde crosslinked, collagen-alkaline phosphatase membranes appeared encapsulated and could be easily removed from the surrounding connective tissue. These membranes appeared slightly thinner than their original thickness and this observation was substantiated by the appearance of the paraffin cross-sections, but otherwise relatively unchanged despite up to 10 weeks in-vivo implantation.

Histological evaluation: All four systems of implants were evaluated histologically. These results were obtained by light microscopy and summarized as follows:

System 1—The only evidence of the graft material was the presence of a slight cellular inflammatory infiltrate in a portion of the histological field with direct evidence of the graft material.

System 2—Glutaraldehyde crosslinked, blank collagen membranes demonstrated a uniform chronic cellular infiltrate in all samples dating from three weeks to 10 weeks. The borders of the grafts are clearly seen and a fibrous capsule is evident surrounding the membrane implants.

System 3—The uncrosslinked collagen-alkaline phosphatase membranes were not evident histologically at 3 weeks implantation. In addition, there was no evidence of any inflammatory response in any of the histologic sections.

Section 4—Cross-linked collagen-alkaline phosphatase membranes demonstrated a complete absence of an inflammatory infiltrate or any inflammatory response in both the graft material and the surrounding connective tissue in all samples ranging from 3 to 10 weeks.

All samples demonstrated a thin, monocellular fibrous capsule. There was no evidence of granulation tissue surrounding the implants in any of the samples. Collagen fibers within all graft implants appeared extremely compacted in a colinear fashion with all fibers oriented in a parallel fashion. This observation may be contrasted with appearance of the graft material in samples from System 2, where collagen fibers appeared more random in their orientation, less compacted, and with spaces between the fibers filled with an inflammatory infiltrate.

EXAMPLE 2

One important application of the phenomenon described in Example 1 is in the production of totally nonflammatory surgical gut sutures. Surgical gut sutures in accordance with the present invention are prepared as follows: gut suture material is swollen in a mild alkali solution (0.1 N NaOH) at a pH of 10.5. The suture material is placed in a solution of human placental alkaline phosphatase in distilled water to allow the enzyme to diffuse into the swollen collagen matrix. After 24 hours of enzyme impregnation into the collagen matrix of the suture material, the suture material is next placed into a neutralizing solution of lactated Ringer's solution to collapse the matrix, thereby retaining the enzyme within the helical collagen macrostructure. The required crosslinking is accomplished by chromic salts or with glutaraldehyde. The degree of biological absorption of the suture material is controlled by the amount of enzyme complexed, either through the concentration of the enzyme bath or the degree of crosslinking.

EXAMPLE 3

Another application of the collagen-alkaline phosphatase conjugates of the present invention involves the use of these novel conjugates as vehicles for drug delivery. Bradley and Wilkes (Bradley, W. G. & Wilkes, G. L., *Biomat., Med. Dev., Art. Org.*, 5 (2), 159–175, 1977) studied several considerations of reconstituted collagen as drug release supports. While collagen can absorb large quantities of drugs within its polymer matrix making it potentially an excellent vehicle for drug delivery, its kinetics of biodegradation and its chronic mild inflammatory response are drawbacks in this same application.

Collagen-alkaline phosphatase conjugates, in the form of gels, sponges, or membranes, are considered to have the ability to maintain the physical continuity of the support matrix and to increase the host acceptance to the drug release polymer. The role of the fibrous capsule in the function of implanted drug-polymer sustained release systems has recently been studied; see Anderson, et. al., Journal of Biomedical Materials Research, Vol. 15, 889–902, 1981. A foreign body reaction which results in the production of a thick fibrous capsule produces a new barrier to the diffusion of the drug. Furthermore, infiltration of the polymer matrix by inflammatory cells may result in the phagocytosis of the support matrix and the drug itself before it can be released.

A variety of drugs may be bound to the non-inflammatory collagen matrix of our invention. Antibiotics, steroids, and other low molecule drugs may be released from these supports. Gels composed of collagen-alkaline phosphatase-calcium hydroxide can be used in endodontics in apexification procedures in early permanent teeth, or as in interim dressing in routine endodontics or in the retreatment of previously treated teeth. Calcium hydroxide is incorporated into such gels by first bringing the gel to a pH of 10.5 with 0.1 N NaOH, then replacing the NaOH with CaOH by dialysis against three changes of saturated calcium hydroxide.

Collagen and collagen-alkaline phosphatase gels saturated with calcium hydroxide ($CaOH_2$) contain approximately $8 \times 10^{-5}$ gram-moles of calcium per cubic centimeter of gel. These gels, when dialyzed against distilled water, display a prolonged, first order (exponential) release of calcium and hydroxyl ions as a function of time.

EXAMPLE 4

The bovine collagen Artegraft, used as an arterial vascular replacement, is rendered non-inflammatory by complexing alkaline phosphatase with the collagen matrix within the graft. The collagen Artegraft, in the uncrosslinked state, is first swollen in 0.1 N NaOH at pH 10.5 for 24 hours at 4° C. The thus-treated collagen is then placed in placental alkaline phosphatase solution in distilled water at 4° C. for 24 hours. The Artegraft can then be crosslinked in glutaraldehyde or starch dialdehyde in the manner as described in U.S. Pat. Nos. 2,900,644 and 3,093,439.

Figure 2:
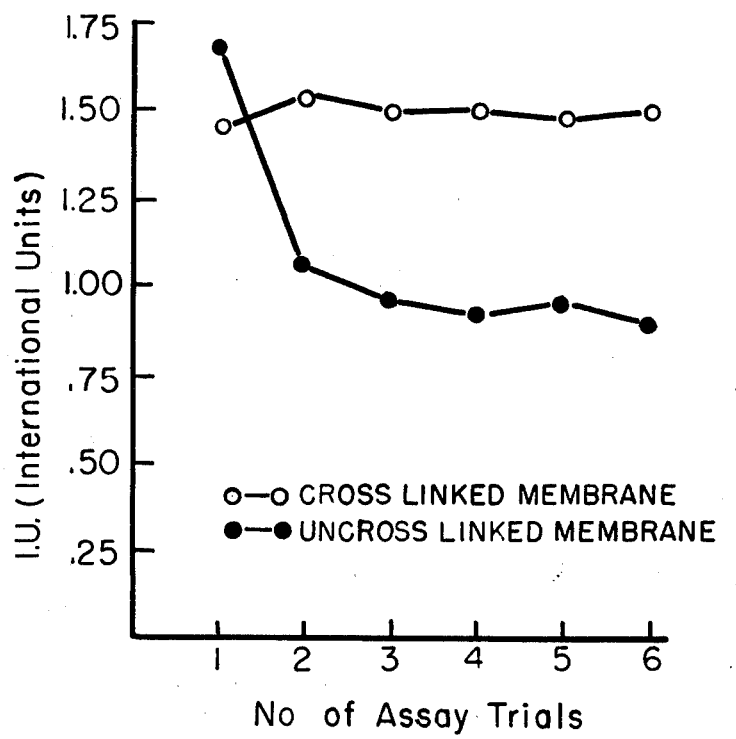
Figure 3:
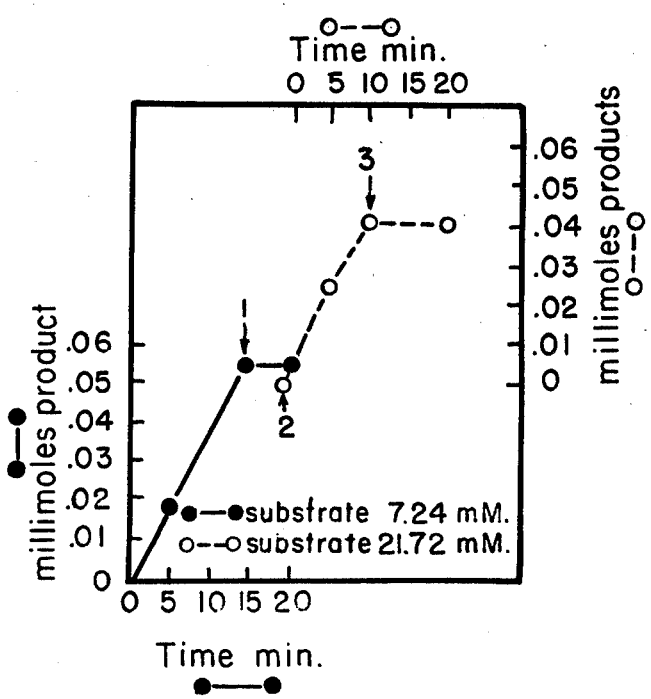

The enzymatic loading of the collagen-phosphatase complexes described in Examples 1, 2, and 3 has been calculated on the basis expressed catalytic activity. Collagen-phosphatase complexes have an expressed volumetric activity of from 25 to 53 International Units per cubic centimeter of dehydrated collagen. On a weight basis, this relates to 10 to 21 milligrams of alkaline phosphatase per cubic centimeter of dehydrated collagen (see FIG. 1). This activity remains constant over repeated in-vitro assay trials of crosslinked collagen-phosphatase membranes (see FIG. 2). Little, if any, enzyme is apparently released from the complexes, as demonstrated by in-vitro enzyme leaching experiments (see FIG. 3). Sufficient crosslinking of the collagen-phosphatase complex, in this case with glutaraldehyde, appears to be an important factor in the stabilization of the collagen-enzyme complex. This observation is substantiated by the in-vitro and in-vivo data presented in this disclosure.

What is claimed is:

1. An inert, non-inflammatory polymeric conjugate of reconstituted collagen crosslinked to form a matrix and complexed with soluble alkaline phosphatase.

2. An article of manufacture consisting essentially of an inert, non-inflammatory polymeric conjugate of reconstituted collagen crosslinked to form a matrix and complexed with soluble alkaline phosphatase.

3. The polymeric complex of claim 1 further including a crosslinking, non-inflammatory inducing amount of glutaraldehyde as a crosslinking agent to confer physical integrity to the polymeric complex.

4. An in vivo implantable membrane made of the polymeric collagen-phosphatase conjugate of claim 1 or 3.

5. A surgical gut suture material made of the polymeric collagen-phosphatase conjugate of claim 1 or 3.

6. A biocompatible, in vivo-injectable gel consisting essentially of the polymeric collagen phosphate conjugate of claim 1 or 3.

7. A biocompatible gel consisting essentially of calcium hydroxide and the polymeric collagen phosphatase conjugate of claim 1 or 3.

8. A drug delivery support consisting essentially of an inert, non-inflammatory polymeric conjugate of reconstituted collagen crosslinked to form a matrix and complexed with a soluble alkaline phosphatase and at least one drug substance compatible with and adapted to separate from said conjugate over a period of several days.

9. A method of forming a collagen-phosphatase conjugate comprising treating a collagen matrix with a solution of soluble alkaline phosphatase until an inert, non-inflammatory a collagen-phosphatase conjugate is formed.

10. The method of claim 9 wherein the collagen is crosslinked prior to said treatment.

11. The method of claim 9 including the additional step of crosslinking the thus formed collagen-phosphatase conjugate with a crosslinking amount of glutaraldehyde.

* * * * *